United States Patent
Venkateshwaran et al.

(10) Patent No.: US 6,365,178 B1
(45) Date of Patent: Apr. 2, 2002

(54) METHOD OF MAKING PRESSURE SENSITIVE ADHESIVE MATRIX PATCHES FOR TRANSDERMAL DRUG DELIVERY USING HYDROPHILIC SALTS OF DRUGS AND HYDROPHOBIC PRESSURE SENSITIVE ADHESIVE DISPERSIONS

(75) Inventors: Srinivasan Venkateshwaran; David Fikstad; Charles D. Ebert, all of Salt Lake City, UT (US)

(73) Assignee: Watson Pharmaceuticals, Inc., Corona, CA (US)

( * ) Notice: Subject to any disclaimer, the term of this patent is extended or adjusted under 35 U.S.C. 154(b) by 0 days.

(21) Appl. No.: 09/764,040

(22) Filed: Jan. 17, 2001

Related U.S. Application Data (63) Continuation of application No. 09/149,523, filed on Sep. 8, 1998, now abandoned, which is a continuation-in-part of application No. 08/706,624, filed on Sep. 6, 1996, now Pat. No. 5,985,317.

(51) Int. Cl.[7] .................................................. A61K 9/70
(52) U.S. Cl. .......................... 424/449; 424/447; 424/448
(58) Field of Search ................................ 424/447, 448, 424/449

(56) References Cited

U.S. PATENT DOCUMENTS

| | | | | |
|---|---|---|---|---|
| 4,409,206 A | * | 10/1983 | Stricker | 424/81 |
| 5,310,359 A | * | 5/1994 | Shah et al. | 424/448 |
| 5,368,860 A | * | 11/1994 | Sunami et al. | 424/448 |
| 5,589,498 A | * | 12/1996 | Mohr et al. | 514/413 |
| 5,985,317 A | * | 11/1999 | Vankateshwaran et al. | 424/449 |

* cited by examiner

*Primary Examiner*—Shelley A. Dodson
(74) *Attorney, Agent, or Firm*—Thorpe North & Western; Phanesh Koneru; Paul B. Tran (57) ABSTRACT

A method of making a pressure sensitive matrix patch for transdermal delivery of a drug is disclosed. The method includes the steps of dissolving a hydrophilic salt form of the drug in the water phase of an aqueous dispersion of a hydrophobic pressure sensitive adhesive, casting the resulting mixture as a thin film, and evaporating the water. The physical stability of the drug in the film is excellent, and crystallization of the drug is inhibited. A method of increasing the transdermal flux of an acidic drug is also disclosed.

48 Claims, 1 Drawing Sheet

Fig. 1

METHOD OF MAKING PRESSURE SENSITIVE ADHESIVE MATRIX PATCHES FOR TRANSDERMAL DRUG DELIVERY USING HYDROPHILIC SALTS OF DRUGS AND HYDROPHOBIC PRESSURE SENSITIVE ADHESIVE DISPERSIONS

CROSS-REFERENCE TO RELATED APPLICATIONS

This application is a continuation of application Ser. No. 09/149,523 filed Sep. 8, 1998 now abandoned, which is a continuation-in-part of application Ser. No. 08/706,624 filed Sep. 6, 1996 now U.S. Pat. No. 5,985,317.

BACKGROUND OF THE INVENTION

This invention relates to methods of preparing pressure sensitive adhesive matrix patch devices for transdermal drug delivery. More particularly, the invention relates to the preparation of pressure sensitive adhesive matrix patches by dissolving hydrophilic salts of hydrophobic drugs that are crystalline at room temperature in aqueous dispersions of hydrophobic pressure sensitive adhesive polymers. These patches are surprisingly free from drug crystals upon drying and exhibit unusually good physical stability without the use of a solubilizing agent or crystal growth inhibitor.

Transdermal delivery of various drugs and pressure sensitive adhesive matrix patches for transdermal delivery of such drugs are well known in the art of drug delivery. These matrix patches include a pressure sensitive adhesive layer for affixing the patch to the skin and for carrying the drug and any excipients that are directly incorporated into this adhesive layer. These adhesive matrix patches also typically include an inert, impervious backing layer and a release liner that is peeled off and discarded before applying the patch to the skin. These patches are distinguished from reservoir patches in that the drug in a reservoir patch is incorporated in a layer or compartment separate from the pressure sensitive adhesive layer. An example of a reservoir transdermal patch is described in U.S. Pat. No. 5,120,546 to Hansen et al.

The polymers used to form pressure sensitive adhesives are well known to those skilled in the art and will be discussed in greater detail below. Since these polymers are hydrophobic in nature, they are typically supplied in liquid form, either dissolved in organic solvents (solvent-based adhesives) or as two-phase aqueous dispersions of water-insoluble polymer particles (water-based adhesives). I. Benedek & J. L. Heymans, Pressure-Sensitive Adhesives Technology 34 (1997).

Drugs or pharmaceutical agents that are incorporated into pressure sensitive adhesive matrix patches are often available as either hydrophobic water-insoluble free drugs or as hydrophilic water-soluble salts. These hydrophilic drug salt derivatives are well known in the art and are often the forms that are developed for oral delivery.

In some patents it is suggested that the hydrophobic free drug form of a drug and the hydrophilic salt form of a drug may be freely substituted in a transdermal pressure sensitive adhesive matrix patch. For example, U.S. Pat. No. 5,149,538 to Granger discloses a pressure sensitive adhesive matrix incorporating opioids or their pharmaceutically acceptable salts, however, no mention is made of the means of manufacture or the specific types of adhesives that might be compatible with such opioid drugs or drug salts. Free form drugs and their corresponding salts will normally differ in their physico-chemical properties such as solubility and hydrophobicity. Therefore, it is unlikely that the free drug and salt forms can be freely substituted in a given adhesive. The free drug form is likely to be insoluble in the water phase of an aqueous emulsion pressure sensitive adhesive, while the hydrophilic salt form is likely to be insoluble in the organic solvents of a solvent-based pressure sensitive adhesive.

It is well known in the art that a transdermal delivery system suitable for one drug or drug form may not be suitable for use with another drug or drug form. For example, U.S. Pat. No. 5,633,009 to Kenealy et al. suggests that azapirones and azapirone salts may be freely interchanged in pressure sensitive matrix patches, but discloses only techniques for incorporating hydrophobic azapirone free base in a solvent-based hydrophobic polyisobutylene adhesive. U.S. Pat. No. 5,589,498 to Mohr et al. suggests that ketorolac and ketorolac salts may be freely substituted in transdermal matrix devices, but only discloses techniques for incorporating hydrophobic ketorolac free acid in a hydrophobic solvent-based pressure sensitive acrylic adhesive and techniques for incorporating hydrophilic ketorolac tromethamine in hydrophilic polymers (hydrogels, polyurethane, or pectin/gelatin blends). These examples serve to illustrate that hydrophilic salt forms of drugs are known in the art to be compatible with water-soluble hydrophilic polymers and hydrophobic drug forms are known to be compatible with solvent-based hydrophobic polymers such as are used in typical pressure sensitive adhesives.

For manufacturing transdernal pressure sensitive matrix patches using hydrophilic drug salts, the hydrophilic salt is commonly converted to the hydrophobic free base This conversion and subsequent incorporation in a solvent-based hydrophobic pressure sensitive adhesive polymer is well known in the art. U.S. Pat. No. 5,002,773 to Keshary et al. describes transdermal delivery of a calcium antagonist compound, "TA-3090." Keshary states that the free base form of TA-3090 can be incorporated in polymeric matrix materials in a higher concentration than the maleate salt of TA-3090 and that the free base form is preferred for transdermal delivery. U.S. Pat. No. 4,201,211 to Chandrasekaran et al. discloses a gelled mineral oil-polyisobutylene skin patch for transdermal delivery that incorporates clonidine free base. Oral clonidine tablets, however, are manufactured with the clonidine hydrochloride salt. U.S. Pat. No. 4,262,003 to Urquhart et al. describes a gelled mineral oil-polyisobutylene-scopolamine free base transdermal patch for the administration of scopolamine base. U.S. Pat. No. 4,956,171 to Chang provides examples of the conversion of buprenorphine salts into buprenorphine free base for incorporation into an organic solvent-based pressures sensitive adhesive. These examples serve to illustrate the conversion of a hydrophilic salt form of a drug into the more hydrophobic free base form to render it compatible for incorporation into a hydrophobic pressure sensitive adhesive matrix patch.

Water-based hydrophobic pressure sensitive adhesives are also known in the art. These are two-phase systems wherein the hydrophobic pressure sensitive adhesive polymer is dispersed as particles in water. U.S. Pat. No. 4,564,010 to Coughlan et al. discloses a water-based pressure sensitive adhesive emulsion film for medical use comprising a base layer laminated to a water-based pressure sensitive adhesive coating formed of a mixture of a polyacrylic latex, an ester resin, and a thickening agent. Coughlan teaches that such films can be used in transdermal delivery systems as peripheral adhesives, with the drug being incorporated in a separate element. The possibility of incorporating the drug and optional permeation enhancers into the water-based pressure sensitive layer is not considered. U.S. Pat. No. 4,409,206 to Stricker et al. discloses a means of manufacturing a patch for transdermal drug delivery using acrylic polymer dispersions. In this invention the acrylic dispersion is dried and the hydrophobic drug substances are then allowed to diff-use into the dried film from drug solutions or suspensions in organic solvents, which are subsequently evaporated. The mixing of a water soluble drug salt in an aqueous dispersion and preparing a polymer matrix film in a single coating and drying step was not recognized or discussed.

The manufacture of transdermal matrix patch devices that use water-based pressure sensitive adhesive dispersions has been contemplated in the art, but the incorporation of hydrophilic salts of crystalline drugs in such dispersions has not been considered. U.S. Pat. No. 5,230,896 to Yeh et al. discloses a transdermal delivery system for administration of nicotine comprising nicotine base, an acrylic polymer adhesive, a stabilizer, and a polyester film backing. It is stated that a nicotine salt is also contemplated in the practice of the invention. Such a nicotine salt is used to reduce volatility of the drug and is formed in situ by addition of acid. Nicotine is an unusual compound in that the free base is quite hydrophilic and is a liquid at room temperature. Both nicotine free base and its salts are very water soluble. U.S. Pat. No. 5,186,938 to Sablotsky et al. describes the use of a water-based emulsion adhesive patch for the transdermal administration of nitroglycerin. Nitroglycerin is not an ionizable salt and is liquid at room temperature with appreciable water solubility.

An important consideration for transdermal delivery of drugs or drug salts that are crystalline at room temperature is ensuring that the drug is dissolved in the pressure sensitive adhesive and does not recrystallize over time once it has been incorporated in the dried adhesive film. If the drug is not physically stable and recrystallization occurs during the shelf-life of the transdermal system, inconsistent in vitro drug release and variable in vivo drug delivery could result, thus making the transdermal system unacceptable for use. Techniques known in the art for preventing the recrystallization of drug substances include the incorporation of solubilizing agents to increase the equilibrium solubility of the drug or addition of crystal growth inhibitors to slow the rate of crystal formation. Examples of these approaches can be found in U.S. Pat. No. 5,336,210 to Hidaka et al., which discloses a physically stabilized estradiol pressure sensitive matrix, and U.S. Pat. No. 5,633,009 to Kenealy et al., which discloses an pressure sensitive adhesive matrix patch for azapirones containing isocetyl alcohol as a solubilizer.

In view of the foregoing, it will be appreciated that providing a method of manufacturing physically stable hydrophobic pressure sensitive adhesive matrix patches for transdermal delivery using hydrophilic crystalline drug salts would be a significant advancement in the art.

BRIEF SUMMARY OF THE INVENTION

It is an object of the present invention to provide a method of making a physically stable pressure sensitive adhesive matrix patch for transdermal drug delivery using a hydrophilic salt of a hydrophobic drug and an aqueous dispersion of hydrophobic pressure sensitive adhesive polymers.

It is another object of the invention to provide a method of making a pressure sensitive adhesive matrix patch using a hydrophilic salt of a hydrophobic drug wherein the drug is rendered physically stable.

It is also an object of the invention to provide a method of increasing transdermal flux of a drug wherein the drug delivery patch is made with a hydrophilic salt of the drug.

These and other objects can be addressed by providing a method of preparing a pressure sensitive adhesive matrix patch device comprising the steps of:

(a) dissolving an effective amount of a hydrophilic salt form of a drug with an aqueous dispersion, comprising a water phase, of a hydrophobic pressure sensitive adhesive and optionally a permeation enhancer, to form a mixture;

(b) film casting the mixture and evaporating the water phase to obtain a hydrophobic pressure sensitive adhesive matrix film having the drug fully dissolved therein and having first and second surfaces thereof; and (c) laminating a release liner to the first surface of the matrix film and a substantially drug-impermeable backing layer to the second surface.

Preferably, the water-based adhesive is an acrylic copolymer, ethylene-vinyl acetate copolymer, or polyisobutylene polymer or copolymer that is a two-phase dispersion of water-insoluble polymer particles in water.

Illustrative drugs that can be incorporated into such patches by this method include albuterol sulfate, ketorolac tromethamine, diclofenac sodium, buspirone HCl, lidocaine HCl, clonidine HCl, and warfarin sodium. The matrix film can further comprise an effective amount is of a permeation enhancer selected from the group consisting of cell envelope disordering compounds, solvents, and mixtures thereof.

A method of inhibiting crystallization of a drug in a pressure sensitive adhesive matrix patch comprises:

(a) dissolving an effective amount of a hydrophilic salt form of the drug with an aqueous dispersion, comprising a water phase, of a hydrophobic pressure sensitive adhesive to form a mixture; and (b) film casting the mixture and evaporating the water phase to obtain a hydrophobic pressure sensitive adhesive matrix film having the drug fully dissolved therein.

A method of increasing transdermal flux of an acidic drug comprises applying a pressure sensitive adhesive matrix patch to skin, wherein the matrix patch is prepared by the steps comprising:

(a) mixing an effective amount of a hydrophilic salt form of the acidic drug with an aqueous dispersion, comprising a water phase, of a hydrophobic pressure sensitive adhesive to form a mixture;

(b) film casting the mixture and evaporating the water phase to obtain a hydrophobic pressure sensitive adhesive matrix film having the acidic drug fully dissolved therein and having first and second surfaces thereof; and (c) laminating a release liner to the first surface of the matrix film and a substantially drug-impermeable backing layer to the second surface.

A method of preparing a drug/adhesive layer of a pressure sensitive adhesive matrix patch device comprises the steps of:

(a) dissolving an effective amount of a hydrophilic salt form of the drug with an aqueous dispersion, comprising a water phase, of a hydrophobic pressure sensitive adhesive to form a mixture; and (b) film casting the mixture and evaporating the water phase to obtain a hydrophobic pressure sensitive adhesive matrix film having the drug fully dissolved therein.

A method of inhibiting crystallization of a drug in a drug/adhesive layer of a pressure sensitive adhesive matrix patch comprises the steps of:

(a) dissolving an effective amount of a hydrophilic salt form of the drug with an aqueous dispersion, comprising a water phase, of a hydrophobic pressure sensitive adhesive to form a mixture; and (b) film casting the mixture and evaporating the water phase to obtain a hydrophobic pressure sensitive adhesive matrix film having the drug fully dissolved therein.

DETAILED DESCRIPTION

Before the present method of making a pressure sensitive adhesive matrix patch for transdermal drug delivery is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition for delivering "a drug" includes reference to two or more of such drugs, reference to "an adhesive" includes reference to one or more of such adhesives, and reference to "a permeation enhancer" includes reference to two or more of such permeation enhancers.

In describing and claiming the present invention, the following terminology will be used in accordance with the definitions set out below.

As used herein, "hydrophilic salt" and similar terms mean an ionic form of a drug or pharmaceutical agent, such as sodium, potassium, ammonium, tromethamine, or other cation salts thereof, sulfate or other anion salts thereof, acid addition salts of basic drugs, and base addition salts of acidic drugs. Illustrative examples of such salts include sodium diclofenac, sodium cromolyn, sodium acyclovir, sodium ampicillin, sodium warfarin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolarnine HBr, and brompheniramine maleate.

As used herein, "effective amount" means an amount of a drug or pharmacologically active agent that is nontoxic but sufficient to provide the desired local or systemic effect and performance at a reasonable benefit/risk ratio attending any medical treatment. An effective amount of a permeation enhancer as used herein means an amount selected so as to provide the selected increase in skin permeability and rate of administration.

As used herein, "drug," "pharmaceutical agent," "pharmacologically active agent," or any other similar term means any chemical or biological material or compound suitable for transdermal administration by the methods previously known in the art and/or by the methods taught in the present invention that induces a desired biological or pharmacological effect. The effect can be local, such as providing for a local anaesthetic effect, or it can be systemic. This invention is not drawn to novel drugs or new classes of active agents. Rather it relates to the mode of making dosage forms of agents or drugs that exist in the state of the art or that may later be established as active agents and that are suitable for delivery by the present invention. Such substances include broad classes of compounds normally delivered into the body, including through body surfaces and membranes, including skin. In general, this includes but is not limited antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral, and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

As used herein, "solvent-based pressure sensitive adhesives" are hydrophobic pressure sensitive adhesives that are dissolved in organic solvents, and "water-based pressure sensitive adhesives" are hydrophobic pressure sensitive adhesives that are water-insoluble and that have been dispersed as water-insoluble particles in water. A pressure sensitive adhesive (PSA) is "(a)n adhesive which adheres to a surface at room temperature by temporary application of pressure alone." Shields, Adhesives Handbook 343 (3d ed., 1984). Typical polymers that have been used to form the basis of pressure sensitive adhesives are natural rubbers, block copolymers, synthetic rubbers (butyl rubber and polyisobutylene), styrene-butadiene rubber (SBR), polyacrylates, D. Satas, Pressure Sensitive Adhesives and Adhesive Products in the United States, in Handbook of Pressure Sensitive Adhesive Technology 4 (D. Satas ed., 2d ed., 1989), ethylene-vinyl acetate copolymers, D. Satas, Miscellaneous Polymers, in Handbook of Pressure Sensitive Adhesive Technology 524 (D. Satas ed., 2d ed., 1989), and silicones, L. A. Sobieski & T. J. Tangney, Silicone Pressure Sensitive Adhesives, in Handbook of Pressure Sensitive Adhesive Technology 508 (D. Satas ed., 2d ed., 1989). The physical state of the adhesive raw materials has been discussed by Benedek and Heymans:

In order to be coated onto the face stock material the adhesive must be in the liquid state. This state may be achieved by melting (hot-melt PSAs), dissolving (solvent-based adhesives), or dispersing (adhesive dispersions) the PSAs. . . . Generally, there are aqueous and solvent-based adhesive solutions, and aqueous or solvent-based adhesive dispersions. The most important are the organic solvent solutions of adhesives (solvent-based adhesives) and the water-based dispersions of adhesives (water-based adhesives).

I. Benedek & L. J. Heymans, Pressure-Sensitive Adhesives Technology 34 (1997).

A dispersion is "a two-phase system in which one phase consists of finely divided particles distributed throughout a bulk substance, the particles being the disperse or internal phase and the bulk substance the continuous or external phase." A. C. Casey, Resin Dispersions, in Handbook of Pressure Sensitive Adhesives 545–546 (D. Satas ed., 2d ed., 1989). The term "latex" is also routinely used to describe such systems in which a polymer is the particulate phase and water is the continuous phase. Generally, there are aqueous and solvent-based adhesive solutions, and aqueous or solvent-based adhesive dispersions. The most important are the organic solvent solutions of adhesives (solvent-based adhesives) and the water-based dispersions of adhesives (water-based adhesives).

These particle dispersions are typically formed by emulsion polymerization of water insoluble monomers. D. Satas, Acrylic Adhesives, in Handbook of Pressure Sensitive Adhesives 435 (D. Satas ed., 2d ed., 1989). As a result, these systems are typically called aqueous emulsion pressure sensitive adhesives, although strictly speaking the polymerized system is no longer an emulsion since the disperse phase is no longer a liquid. Examples of such emulsion polymerized adhesives include hydrophobic acrylic copolymer adhesives (e.g. National Starch NACOR 72-9965, Monsanto GELVA 2484, Morton International MORSTICK 214, and Rohm & Haas ROBOND PS-20), ethylene-vinyl acetate copolymer adhesives (e.g. National Starch EVA-TAK 33-4060), or styrene-butadiene rubber adhesives (e.g. National Starch NACOR 72-8725, and Dow Latex PSA 578A). Pressure sensitive adhesives can also be obtained by compounding emulsion-polymerized dispersions of hydrophobic elastomeric polymers (e.g. BASF ACRONAL A217) with tackifiers that are water soluble (e.g. polyvinylmethyl ether; BASF LUTONAL M40) or that are water insoluble particle dispersions in water (e.g. polyvinylisobutyl ether; BASF LUTONAL I 65 D).

Dispersions of hydrophobic pressure sensitive adhesive polymers in water can also be formed by polymerizing the monomers (neat or solution polymerization), then removing the solvent and dispersing the polymer in water with the aid of surfactants (e.g. Lord PIB 500 and Lord BL-100).

As used herein, "physical stability" of a drug in a matrix patch includes the lack of recrystallization of the drug in the dried adhesive layer of the patch.

As used herein, "permeation enhancer," "penetration enhancer," "chemical enhancer," or similar terms refers to compounds and mixtures of compounds that enhance the permeation of a drug across the skin.

Chemical enhancers are comprised of two primary categories of components, i.e., cell-envelope disordering compounds and solvents or binary systems containing both cell-envelope disordering compounds and solvents. The latter are well known in the art, e.g. U.S. Pat. Nos. 4,863,970 and 4,537,776, incorporated herein by reference.

Cell envelope disordering compounds are known in the art as being useful in topical pharmaceutical preparations. A comprehensive list of these compounds is set forth in European Patent Application 43,738, published Jun. 13, 1982, which is incorporated herein by reference. Examples of cell envelope disordering compounds that can be used as enhancers, without limitation, include saturated and unsaturated fatty acids and their esters, alcohols, monoglycerides, acetates, diethanolamides, and N,N-dimethylamides, such as oleic acid, propyl oleate, isopropyl myristate, glycerol monooleate, glycerol monolaurate, methyl laurate, lauryl alcohol, lauramide diethanolamide, and mixtures thereof. Saturated and unsaturated sorbitan esters, such as sorbitan monooleate and sorbitan monolaurate, can also be used. It is believed that any cell envelope disordering compound is useful for purposes of this invention.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

What has hitherto gone unrecognized, and is the subject of the present invention, is a method for manufacturing a pressure sensitive adhesive matrix device for transdermal drug delivery by adding the hydrophilic salt form of the hydrophobic free drug directly to a water-based adhesive (a two-phase aqueous dispersion of a hydrophobic pressure sensitive adhesive polymer) and evaporating the water phase. The salt form of the drug is usually hydrophilic and insoluble in organic-solvent-based adhesives and cannot be incorporated into organic-solvent-based adhesive patches to provide clinically meaningful skin flux. Hydrophilic salt forms of hydrophobic drugs are generally readily soluble in aqueous dispersions of hydrophobic pressure sensitive adhesives because the carrier is water, not an organic solvent. Such salt forms of drugs have previously had to be converted to the more hydrophobic free acid or free base form to be soluble and/or compatible in the organic-solvent-based adhesive to obtain clinically meaningful skin flux. This prior procedure required additional process steps, wherein the drug was converted from the FDA-approved salt form to an unapproved free acid or free base form, thus introducing additional regulatory and/or toxicological hurdles to developing a matrix patch. These problems can be avoided by formulating the salt form of the drug in a water-based pressure sensitive adhesive. As will be shown in more detail herein, the drugs incorporated into patches prepared in this way are surprisingly physically stable. The present method also has safety and toxicological advantages since the carrier is water and not an organic solvent.

More importantly, systems manufactured in this manner are free from drug crystals upon drying and have surprising physical stability relative to systems prepared using the conventional manufacturing technique using hydrophobic free drug forms and organic solvent-based pressure sensitive adhesives. Using this technique, effective amounts of a crystalline drug or pharmaceutical agent can be dissolved in the carrier of a hydrophobic pressure sensitive adhesive, and the drug will remain dissolved in the dried laminate without the use of a solubilizing agent.

Drug flux from these patches containing dissolved drug is better than the drug flux from patches that contain undissolved crystalline drug particles in the matrix and is comparable to or better than the skin flux obtained from patches manufactured using the conventional technique by combining the hydrophobic free drug form and a solvent-based adhesive. Comparable skin flux is indicated by relative flux ratios from 0.4 or greater. Most importantly, patches manufactured in this manner have improved physical stability relative to systems prepared using the conventional manufacturing technique. Using the technique described herein, effective amounts of a crystalline drug or pharmaceutical agent can be dissolved in the carrier of a hydrophobic pressure sensitive adhesive, and the drug will remain dissolved in the dried laminate without the use of a solubilizing agent.

Figure 1:
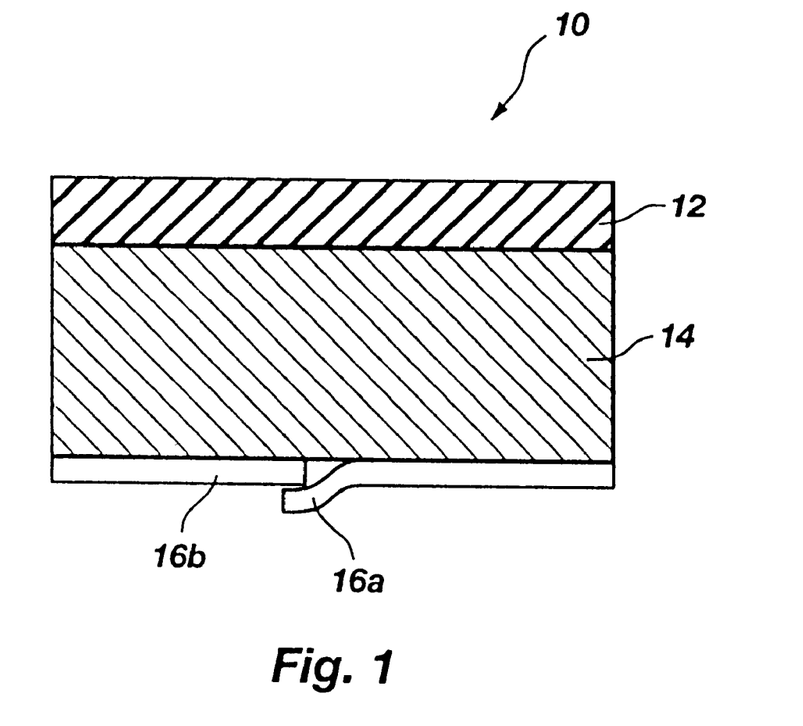
FIG. 1 shows a schematic sectional view through an illustrative device according to the present invention.

FIG. 1 shows an exemplary matrix patch 10 that is compatible with the present invention. The patch 10 is a laminated composite wherein the backing layer 12 forms the top surface of the composite. The drug-containing adhesive matrix layer 14 is immediately below and adjacent to the backing layer. Prior to use, the laminate also includes a strippable protective release liner. The release liner can be in the form of two sheets, 16a and 16b, the first sheet 16a partially overlapping the second sheet 16b. Additional structural layers can also be present.

The backing layer, which adheres to the drug-containing adhesive layer, serves as the upper layer of the device during use and functions as the primary structural element of the device. The backing layer is made of a sheet or film of a preferably flexible elastomeric material that is substantially impermeable to the drug and any enhancer that may be present. This backing layer is typically about 0.001–0.004 inch in thickness and is preferably of a material that permits the device to follow the contours of the skin such that it can be worn comfortably on any skin area including joints or other areas of flexure. In this way, in response to normal mechanical strain, there is little or no likelihood of the device disengaging from the skin due to differences in the flexibility or resiliency of the skin and the device. Examples of polymers useful for the backing layer are polyethylene, polypropylene, polyesters, polyurethanes, polyethylene vinyl acetate, polyvinylidene chloride, block copolymers such as PEBAX, and the like. The backing layer can also comprise laminates of one or more of the foregoing polymers.

The release liner is a disposable element that serves only to protect the device prior to application to the skin. Typically, the release liner is formed from a material impermeable to the drug, enhancer, and other components of the device, and is easily strippable from the pressure sensitive adhesive. Release liners can generally be made of the same materials as the backing layer.

The drug-containing adhesive matrix layer can, in addition to the adhesive, drug, and optional permeation enhancer, also contain other optional ingredients, such as thickeners, excipients, tackifiers, preservatives, defoamers, antioxidants, and the like, which are materials without pharmacological activity that are suitable for administration in conjunction with the presently disclosed and claimed compositions. Such materials are pharmaceutically acceptable in that they are nontoxic, do not interfere with drug delivery, and are not for any other reasons biologically or otherwise undesirable. The pressure sensitive adhesives used in accordance with the present invention must also be pharmaceutically acceptable.

Adhesive Matrix Preparation

Pressure sensitive adhesive matrix systems described herein were prepared as follows. First, the solids content of a water-based or solvent-based adhesive in liquid form was determined by placing a known weight of liquid in a weighed aluminum dish and evaporating the solvents overnight in a 70° C. convection oven. The content of solid adhesive in the liquid was calculated by dividing the adhesive solid weight after drying by the initial total liquid weight. In some cases, the polyisobutylene (PIB) adhesives were prepared from polyisobutylene solids. The solid PIB was first dissolved in heptane to achieve a final solid content of about 30% by weight, and then the exact solid content was determined as described above. Next, a weighed quantity of adhesive liquid was added to a glass bottle, and the solid adhesive weight was calculated from the known solid fraction of the given adhesive liquid. The drug substance (hydrophilic salt or free drug form) was weighed and added to the adhesive solution in a quantity necessary to achieve a selected dry matrix film composition. The liquid containing the adhesive polymer drug substance was then mixed overnight. In some cases, the drug substance dissolved completely in the mixture. In other cases, the drug did not completely dissolve, resulting in a liquid containing some drug crystals dispersed in the solution. After mixing, approximately 8 ml of the solution was dispensed on a silanized polyester release liner and film cast using a casting knife with a gap size appropriate to achieve a final dried thickness of approximately 0.05–0.1 mm. The cast was dried in a 70° C. convection oven for 15–30 minutes to yield a dried matrix onto which an 0.08 mm thick polyethylene backing film was laminated. These matrix systems were then used to conduct in vitro skin flux experiments as described below.

Skin Flux Studies

In vitro skin flux studies were conducted using human cadaver epidermal membrane in modified Franz non-jacketed diffusion cells. Merrit & Cooper, 1 J. Controlled Release 161 (1984). The epidermal membrane (stratum corneum and epidermis) was separated from whole skin (epidermal membrane and dermis) by the heat-separation method of Kligman & Christopher, 88 Arch. Dermatol. 702 (1963). This method involves the exposure of the fullthickness skin to water at 60° C. for 60 seconds. After this period, the epidermal membrane was gently peeled from the dermis and stored in aluminum foil at −5 ° C. Prior to skin permeation experiments, the silanized release liner was removed from the adhesive matrix system, and the adhesive was affixed to the stratum corneum side of the thawed epidermal membrane, which was then cut to an appropriate size and placed between the two halves of the diffusion cell with the stratum corneum facing the donor compartment.

The receiver compartment was filled with water or an aqueous buffer appropriate to maintain sink conditions for the drug. All receiver media included 0.02% (w/w) sodium azide to inhibit bacterial growth. The diffusion cell was placed in a temperature controlled circulating water bath calibrated to maintain the surface temperature of the skin at 32° C. The receiver compartment was constantly stirred by a magnetic stir bar in the receiver compartment agitated by a magnetic stirring module placed under the water bath. At predetermined sampling intervals, the entire contents of the receiver compartment were collected for drug quantitation, and the receiver compartment was filled with fresh receiver solution, taking care to eliminate any air bubbles at the skin/solution interface.

The cumulative amount of drug permeated per unit area at any time t ($Q_t$, $\mu g/cm^2$) was determined according to the following equation:

$$Q_t = \sum_{t=0}^{t} \frac{C_t V}{A}$$

where $C_t$ ($\mu g/cm^3$) is the concentration of the receiver compartment at sample time t (hours), V is the volume of the receiver compartment of the diffusion cell (6.3 cm$^3$), and A is the diffusional area of the cell (0.64 cm$^2$).

EXAMPLE 1

Buspirone is an azapirone anxiolytic drug, and the FDA-approved form of the drug is the hydrochloride (HCl) salt. Pressure sensitive adhesive systems were prepared using the methods described above with buspirone hydrochloride and buspirone free base in several different adhesives: (1) MA-24 (Adhesives Research, Glen Rock, Pa.), an organic solvent-based PIB adhesive; (2) PIB-500 (Lord Corporation, Pompano Beach, Fla.), a comparable water-based PIB; (3) DUROTAK 2979 (National Starch and Chemical Company, Bridgewater, N.J.), an organic solvent-based acrylic adhesive; (4) NACOR 72-9965 (National Starch and Chemical Company), a comparable water-based acrylic. In each case, the drug substance was mixed with the liquid adhesive in quantities sufficient to obtain a concentration of 5% (w/w) drug in the dried film after film casting.

The hydrophobic buspirone free base dissolved readily in the organic solvent-based adhesives and the dried films were visibly homogeneous and free from drug crystals. The hydrophilic buspirone hydrochloride salt did not dissolve in the organic solvent solution and the resulting dried films were filled with drug crystals that were visible to the naked eye. Several compatible co-solvents, such as methanol, acetone, ethyl acetate, toluene, and chloroform, were tried in efforts to dissolve the hydrophilic buspirone hydrochloride in the organic solvents of the solvent-based adhesives; however, none of these were successful at producing a dried film free from drug crystals.

To incorporate the water insoluble buspirone free base in the water-based adhesive systems, methanol was needed as a volatile co-solvent. In contrast, the hydrophilic buspirone hydrochloride salt dissolved readily in the water-based dispersions of the hydrophobic adhesives. Surprisingly, upon casting and drying of the water-based adhesive dispersions, no crystals were found in the dried film.

The resulting systems were stored at room temperature and observed microscopically for the presence of drug crystals. The observations for the systems prepared with the PIB adhesive are summarized in Table 1 and observations for the systems prepared with the acrylic adhesives are summarized in Table 2.

TABLE 1

PIB Matrix Systems

| Adhesive | Drug | Observations |
|---|---|---|
| MA-24 (Organic Solvent-based PIB) | 5% Buspirone Free Base | Crystals form within 11 days. |
|  | 5% Buspirone HCl | Drug does not dissolve and no compatible co-solvents have been identified, crystals present immediately after preparation. (See Example 3) |
| Lord PIB-500 (Water-based PIB) | 5% Buspirone Free Base | Crystals form within 3 days. |
|  | 5% Buspirone HCl | No crystals observed after 7 weeks. |

TABLE 2

Acrylic Matrix Systems

| Adhesive | Drug | Observations |
|---|---|---|
| DURO-TAK 2979 (Organic Solvent-based Acrylic) | 5% Buspirone Free Base | Crystals form within 6 days. |
|  | 5% Buspirone HCl | Drug does not dissolve and no compatible co-solvents have been identified; crystals are present immediately after preparation. |
| NACOR 72-9965 (Water-based Acrylic) | 5% Buspirone Free Base | Crystals observed within 16 days. |
|  | 5% Buspirone HCl | No crystals have been observed after 59 weeks of storage |

There are four possible combinations of drug form and adhesive form: free base+organic solvent-based PSA; salt+organic solvent-based PSA; free base+water-based PSA; salt+water-based PSA. Only the combination of salt+water-based PSA produces physically stable systems at the concentration tested. These results show that the manufacture of buspirone pressure sensitive matrix systems by mixing buspirone hydrochloride salt with a water-based adhesives confers an unexpected advantage with respect to the physical stability of the dried matrix and allows for production of stable matrix systems at relatively high drug concentration (5% w/w) without use of a solubilizer. This is unexpected in light of Kenealy et al., U.S. Pat. No. 5,633,009, wherein it was shown that a solubilizer is necessary to produce a stable pressure sensitive matrix using buspirone free base in an organic solvent-based PSA, even at relatively low drug concentrations (1.5% w/w).

EXAMPLE 2

Pressure sensitive matrix systems with buspirone free base were prepared according to the procedure of Example 1 in two organic solvent-based acrylic copolymer adhesives, TSR (Sekisui Chemical Company, Osaka, Japan) and DURO-TAK 2516 (National Starch and Chemical Co.), at concentrations equivalent to 1% or 2% (w/w) of the HCl salt. The HCl salt did not dissolve completely in the organic solvents of these solvent-based adhesives, and the final dried casts contained visible solid drug crystals in the adhesive matrix. A matrix system with Buspirone HCl at 1% or 2% (w/w) was prepared in a comparable water-based acrylic copolymer adhesive dispersion, NACOR 72-9965. The HCl salt dissolved completely in this water-based adhesive dispersion, and the dried adhesive matrix was visibly free of drug crystals. The results of in vitro skin flux experiments using these systems are summarized in Tables 3–5.

TABLE 3

| | No. | In vitro Permeation of Buspirone[a] | | |
|---|---|---|---|---|
| Skin | Cells | TSR/salt[b] | TSR/base[c] | NACOR/salt[d] |
| 1 | 5 | 1.53 ± 0.70 | 15.54 ± 7.01 | 3.18 ± 0.50 |
| 2 | 5 | 4.46 ± 1.55 | 21.22 ± 4.36 | 9.16 ± 1.84 |
| 3 | 5 | 9.17 ± 4.95 | 27.40 ± 4.06 | 12.26 ± 2.67 |
| 4 | 5 | 4.02 ± 1.09 | 17.96 ± 1.37 | 9.54 ± 1.86 |
| Total | 20 | 4.80 ± 3.75 | 20.53 ± 6.25 | 8.53 ± 3.82 |

[a]Mean ± SD, $\mu g/(cm^2 \ast 24\ h)$
[b]TSR/buspirone HCl = 99%/1% (w/w)
[c]TSR/buspirone free base = 99.1%/0.9% (w/w)
[d]NACOR 72-9965/buspirone HCl 99%/1% (w/w)

TABLE 4

| Skin | No. Cells | In vitro Permeation of Buspirone[a] | | |
|---|---|---|---|---|
| | | TSR/salt[b] | TSR/base[c] | NACOR/salt[d] |
| 1 | 5 | 15.11 ± 2.42 | 71.48 ± 2.94 | 56.13 ± 4.59 |
| 2 | 5 | 6.57 ± 0.58 | 43.76 ± 7.02 | 34.08 ± 1.71 |
| 3 | 5 | 9.38 ± 1.78 | 63.17 ± 2.27 | 32.30 ± 6.35 |
| 4 | 5 | 13.49 ± 3.46 | 67.81 ± 4.81 | 48.82 ± 6.87 |
| Total | 20 | 11.14 ± 4.05 | 61.55 ± 11.77 | 42.83 ± 11.35 |

[a]Mean ± SD, $\mu g/(cm^2 * 24\ h)$
[b]TSR/buspirone HCl 98%/2% (w/w)
[c]TSR/buspirone free base = 98.2%/1.8% (w/w)
[d]NACOR 72-9965/buspirone HCl 98%/2% (w/w)

TABLE 5

| Skin | No. Cells | In vitro Permeation of Buspirone[a] | | |
|---|---|---|---|---|
| | | DURO-TAK/salt[b] | DURO-TAK/base[c] | NACOR/salt[d] |
| 1 | 5 | 15.9 ± 1.3 | 76.5 ± 5.3 | 31.8 ± 8.8 |
| 2 | 5 | 11.2 ± 2.2 | 87.3 ± 13.5 | 24.5 ± 7.2 |
| 3 | 5 | 8.9 ± 2.0 | 66.7 ± 7.1 | 28.3 ± 3.8 |
| 4 | 5 | 13.0 ± 1.2 | 62.5 ± 30.3 | 28.2 ± 6.0 |
| Total | 20 | 12.3 ± 3.1 | 73.2 ± 18.6 | 28.2 ± 6.7 |

[a]Mean ± SD, $\mu g/(cm^2 * 24\ h)$
[b]DURO-TAK 2516/buspirone HCl = 98%/2% (w/w)
[c]DURO-TAK/buspirone free base = 98.2%/1.8% (w/w)
[d]NACOR 72-9965/buspirone HCl 98%/2% (w/w)

Permeation from the matrix prepared with the salt form of the drug and the water-based adhesive wherein the drug was dissolved and physically stable, was two to four times that obtained from the matrix prepared with the salt form of the drug in the comparable organic solvent-based adhesive, wherein the drug was present as a mixture of dissolved and undissolved drug. In addition, permeation from the matrix prepared with the salt form of the drug and the water-based adhesive was comparable to permeation from the matrix prepared using the more conventional technique of mixing the hydrophobic free base and the organic solvent-based adhesives.

EXAMPLE 3

In this example, a buspirone transdermal delivery device was prepared according to techniques known in the art. It has been claimed that devices can be prepared in this manner using either buspirone free base or buspirone salts such as buspirone HCl, therefore devices were prepared using both forms of the drug for comparison.

Preparation with Buspirone Free Base

A transdermal buspirone delivery device was prepared using buspirone free base according to the technique described in WO 97/37659 (Example 3) and U.S. Pat. No. 5,633,009 (Example 1). Buspirone free base (0.70±0.01 g) was dissolved in 9.20 g of a prior art solvent (acetone, 99.5%+; Aldrich; Milwaukee, Wis.). This buspirone free base solution was combined with 6.1±0.01 g of isocetyl alcohol (Condea-Vista; Austin, Tex.). The buspirone free-base/acetone/isocetyl alcohol mixture was blended with a commercial organic solution PIB adhesive (MA-24, Adhesives Research, Glen Rock, Pa.). The buspirone free base/acetone/isocetyl alcohol/PIB adhesive mixture was cast on a release coated polymer film (Rexam Release Technologies; W. Chicago, Ill.) to obtain a dried coating weight of approximately 10 mg/ml. This film was dried at 60° C. in a convection oven for 30 minutes and the dried film was laminated to a polyester film laminate (SCOTCHPACK #1012, 3M Pharmaceuticals; St. Paul, Minn.). The composition of the dried pressure sensitive adhesive matrix was PIB adhesive/buspirone free base/isocetyl alcohol 86/1.5/12.5% (w/w).

The resulting laminate was stored at room temperature and 40° C./70%RH for 3 weeks and the stability of buspirone in the transdermal device was evaluated microscopically. No recrystallization of buspirone occurred, thus supporting the teaching of WO 97/37659 and U.S. Pat. No. 5,633,009 when applied to the use of buspirone free base.

Preparation with Buspirone Hydrochloride Salt

A transdermal buspirone delivery device was prepared using buspirone hydrochloride salt according to the technique described in WO 97/37659 (Example 3) and U.S. Pat. No. 5,633,009 (Example 1). This approach is based on the premise that all salts of the base compound are included in the term buspirone (U.S. Pat. No. 5,633,009 at Col. 8, Lines 23–25). Buspirone hydrochloride (0.70 g) was added to 9.2 g of acetone (99.5%+; Aldrich; Milwaukee, Wis.). The hydrophilic buspirone hydrochloride salt did not completely dissolve in this solvent. The buspirone hydrochloride/acetone mixture was combined with 6.1 g of isocetyl alcohol (Condea-Vista; Austin, Tex.). The hydrophilic buspirone hydrochloride did not completely dissolve in this mixture. The buspirone hydrochloride/acetone/isocetyl alcohol mixture was blended with a commercial organic solvent-based PIB adhesive (MA-24, Adhesives Research, Glen Rock, Pa.). The hydrophilic buspirone hydrochloride also did not completely dissolve in this mixture. The buspirone hydrochloride/acetone/isocetyl alcohol/PIB adhesive mixture was cast on a release coated polymer film (Rexam Release Technologies, W. Chicago, Ill.) to obtain a dried coating weight of approximately 10 mg/ml. This film was dried at 60° C. in a convection oven for 30 minutes and the dried film was laminated to a polyester film laminate (SCOTCHPACK #1012, 3M Pharmaceuticals; St. Paul, Minn.). The composition of the dried pressure sensitive adhesive matrix film was PIB adhesive/buspirone hydrochloride/isocetyl alcohol 86/1.5/12.5% (w/w).

The resulting laminate was filled with buspirone crystals that were visible to the naked eye and upon microscopic examination, thus demonstrating that isocetyl alcohol is not an effective solubilizer for buspirone hydrochloride in this matrix system. This result does not support the teaching of WO 97/37659 and U.S. Pat. No. 5,633,009 when applied to the use of buspirone hydrochloride in a solvent-based PSA.

The process described above was repeated using several other solvents, and the results are summarized in Table 6.

TABLE 6

| Solvent | Results |
|---|---|
| Acetone | Buspirone hydrochloride (0.7 g) did not dissolve in acetone (12.0 g), or in the acetone/isocetyl alcohol/solvent solution PIB adhesive mixture and the resulting cast contained extensive buspirone crystals. |
| Water | Buspirone hydrochloride (0.7 g) dissolved in water (1.5 g), but water/isocetyl alcohol/adhesive solution phase separated. The resulting cast contained distinct regions that were apparent upon visual and microscopic examination. Buspirone was present only in what appears to have been the water-rich phase and crystallized extensively within 24 hours after casting. |
| Toluene | Buspirone hydrochloride (0.7 g) did not dissolve in toluene (12.0 g), or in the toluene/isocetyl alcohol/solvent |

TABLE 6-continued

| Solvent | Results |
| --- | --- |
| | solution PIB adhesive mixture and the resulting cast contained extensive buspirone crystals. |
| Methanol | Buspirone hydrochloride (0.7 g) dissolved in methanol (12.0 g), but methanol/isocetyl alcohol/solvent solution PIB adhesive phase separated. It was impossible to cast this mixture because the adhesive formed a gel-like ball surrounded by the methanol/drug solution. |
| Chloroform | Buspirone hydrochloride (0.7 g) dissolved in chloroform (12.0 g) and in the chloroform/isocetyl alcohol mixture. The addition of the solvent solution PIB adhesive resulted in precipitation of buspirone, and the resulting cast contained extensive buspirone crystals. |
| Ethyl acetate | Buspirone hydrochloride (0.7 g) did not dissolve in ethyl acetate (12.0 g), or in the ethyl acetate/isocetyl alcohol/solvent solution PIB adhesive mixture, and the resulting cast contained extensive buspirone crystals. |

This example shows that buspirone hydrochloride salt cannot be successfully substituted for buspirone free base in the examples of WO 97/37659 and U.S. Pat. No. 5,633,009. The teaching that buspirone recrystallization is inhibited using solubilizers such as isocetyl alcohol appears to be operative for the use of buspirone free base, but is not applicable to the use of a hydrophilic buspirone salt. This contrasts with the results obtained herein in Examples 1 and 2 wherein hydrophobic pressure sensitive adhesive laminates were manufactured using the method of the present invention with the hydrophilic buspirone hydrochloride salt and an aqueous dispersion of a hydrophobic pressure sensitive adhesive. The present method not only provides a method of successfully manufacturing physically stable pressure sensitive adhesive matrix transdermal delivery devices, but also makes unnecessary the use of a solubilizing agent.

EXAMPLE 4

Albuterol is a beta$_2$-adrenergic bronchodilator available in the hydrophobic free drug form and also as a hydrophilic sulfate salt. Pressure sensitive adhesive systems were prepared with albuterol sulfate and albuterol free base at 10% (w/w) concentrations in two different adhesives:

(1) Sekisui TSR, an organic solvent-based acrylic/vinylpyrrolidone copolymer adhesive solution,
(2) National Starch NACOR 9965, a water based acrylic copolymer adhesive dispersion with 5% (w/w) KOLLIDON 90F (a vinylpyrrolidone homopolymer) as a thickening agent.

The resulting systems were stored at 40° C./75% RH and observed microscopically for the presence of drug crystals. These observations are summarized in Table 7.

TABLE 7

| Adhesive | Drug | Observations |
| --- | --- | --- |
| TSR (Organic Solvent-based Acrylic) | 10% Albuterol Free Base | Crystals were observed at 59 weeks of storage. |
| NACOR 9965 (Water-based Acrylic) | 10% Albuterol Sulfate | No crystals were observed at 59 weeks of storage. |

This example shows that it is feasible to make hydrophobic pressure sensitive adhesive matrix patches with the hydrophilic albuterol sulfate salt and a water based dispersion of a hydrophobic acrylic copolymer pressure sensitive adhesive. Furthermore, this example shows that a system manufactured in this manner has an unexpected physical stability advantage relative to a system manufactured with the hydrophobic albuterol free base and a comparable organic solvent-based pressure sensitive adhesive solution. These results show that the manufacture of albuterol pressure sensitive matrix systems by mixing albuterol sulfate salt with a water based adhesives confers an unexpected advantage with respect to the physical stability of the dried matrix and allows for production of stable matrix systems at relatively high concentration (10% w/w) without use of a solubilizing agent.

EXAMPLE 5

Ketorolac is an acidic non-steroidal anti-inflammatory drug, and the FDA-approved form of ketorolac is the hydrophilic tromethamine salt (2-amino-2-hydroxymethyl-1,3-propanediol). Pressure sensitive matrix systems with ketorolac free acid and ketorolac tromethamine were prepared in an organic solvent-based acrylic pressure sensitive adhesive (TSR) at concentrations equivalent to 1% (w/w) of the tromethamine salt. The tromethamine salt did not completely dissolve in the organic solvent system, and the dried matrix contained crystallized drug in an acrylic adhensive matrix. Ketorolac free acid completely dissolved in the organic solvent system, and the dried matrix was visually free of any crystals. An adhesive matrix system was also prepared using ketorolac tromethamine at 1% (w/w) and a comparable water-based acrylic adhensive dispersion (NACOR 72-9965). The tromethamine salt dissolved completely in the water/emulsion system, and the dried matrix was free of drug crystals. The results of in vitro skin flux experiments using these matrix systems are summarized in Table 8.

TABLE 8

| | In vitro Permeation of Ketorolac[a] | | |
| --- | --- | --- | --- |
| Skin | TSR/salt[b] | TSR/acid[c] | NACOR/salt[d] |
| 1 | 2.78 ± 1.78 (n = 5 cells) | 2.18 ± 0.85 (n = 4 cells) | 7.34 ± 3.75 (n = 5 cells) |
| 2 | 0.52 ± 0.23 (n = 5) | 1.04 ± 0.28 (n = 5) | 2.29 ± 0.46 (n = 5) |
| 3 | 0.72 ± 0.29 (n = 5) | 1.72 ± 0.72 (n = 5) | 8.13 ± 1.74 (n = 5) |
| 4 | 0.59 ± 0.37 (n = 5) | 1.56 ± 0.41 (n = 5) | 2.63 ± 0.87 (n = 5) |
| Total | 1.15 ± 1.29 (n = 20) | 1.59 ± 0.67 (n = 19) | 5.10 ± 3.35 (n = 20) |

[a]Mean ± SD, $\mu g/(cm^2*24\ h)$
[b]TSR/ketorolac tromethamine = 99%/1% (w/w)
[c]TSR/ketorolac free acid = 99%/0.7% (w/w)
[d]NACOR 72-9965/ketorolac tromethamine = 99%/1% (w/w)

These results demonstrate that physically stable pressure sensitive matrix films can be prepared using the technique of combining the hydrophilic tromethamine salt form of ketorolac and water based adhesive dispersion. The matrix systems manufactured in this manner exhibit significantly improved skin flux relative to systems containing undissolved drug crystals manufactured by combining the tromethamine salt with a comparable solvent-based adhesive. In addition, the matrix systems manufactured using the salt and the water adhesive dispersion have significantly improved skin flux relative to systems produced using the conventional technique of combining the hydrophobic free acid form with a comparable organic solvent-based pressure sensitive adhesive.

EXAMPLE 6

In this example, a ketorolac transdermal delivery device was prepared according to techniques described in the art. It is claimed in the art that devices can be prepared in this manner using either ketorolac free acid or ketorolac salts such as ketorolac tromethamine. Therefore devices were prepared using both forms of the drug for comparison.

Preparation with Ketorolac Free Acid

Transdermal patches with 10% ketorolac free acid were prepared according to the procedure described in U.S. Pat. No. 5,589,498 (Example 2). Ketorolac free acid (1.65 g) was added to 0.64 g of propylene glycol (Sigma, Lot #27H1179) and 0.67 g isopropyl myristate (Nikko Chemicals, Lot #4123). The mixture was added to 41.05 g of a pressure sensitive acrylic copolymer adhesive in an organic solution (DURO-TAK 2852, formerly DURO-TAK 9852; National Starch and Chemical, Lot 7898-117-1, 33.5% solids). The solution was left to mix for 12 hours on a rolling mill. The ketorolac acid-enhancer-adhesive mixture formed a homogeneous solution. The drug-enhancer-adhesive mixture was then cast on SCOTCHPAK 1012 polyester backing film (3M, Lot #138) with a 40 mil (1,016 $\mu$m) casting knife. The solvent in the adhesive solution was evaporated at room temperature for 30 minutes and then in an oven at 100° C. for 15 minutes. The resulting adhesive film was laminated to a release liner (SCOTCHPAK #1022, Lot 640). The resulting transdermal laminate was cut into 0.71 cm$^2$ disks for in vitro evaluation. The adhesive matrix was visibly homogeneous and free from crystals upon microscopic examination.

In vitro skin flux of ketorolac from this patch (with 10% ketorolac, 8% enhancer (propylene glycol/isopropyl myristate), and 82% adhesive solids was 25.4±4.2 $\mu$g/cm$^2$/h (Mean±SD, n=2/10 skins/diffusion cells). The average cumulative amount of ketorolac released after 24 hours was 583.3±94.6 $\mu$g/cm$^2$. These results are in excellent agreement with U.S. Pat. No. 5,589,498 (Example 2), which discloses a flux of 21.6±3.6 $\mu$g/cm$^2$/h and a 24 hour cumulative release of 461.7±83.8. These results support the teaching of U.S. Pat. No. 5,589,498 when applied to the use of the ketorolac acid.

Preparation with Ketorolac Tromethamine

Transdermal patches with 10% ketorolac (on a free acid basis) were prepared with ketorolac tromethamine salt according to the procedure described in U.S. Pat. No. 5,589,498 (Example 2). This approach is based on the premise that all pharmaceutically accepted salts of the ketorolac free acid compound are included in the term ketorolac (U.S. Pat. No. 5,589,498 at Col. 4, Lines 46–51). Ketorolac tromethamine salt (2.10 g) was added to 0.56 g of propylene glycol (Sigma, Lot #27H1179) and 0.56 g isopropyl myristate (Nikko Chemicals, Lot #4123). The mixture was added to 32.6 g of a pressure sensitive acrylic copolymer adhesive in an organic solution (DURO-TAK 2852, formerly DURO-TAK 9852; National Starch and Chemical, 33.5% solids). The solution was left to mix for 12 hours on a rolling mill. The ketorolac tromethamine does not dissolve in the enhancer-acrylic adhesive solution. The drug-enhancer-adhesive mixture was then cast on SCOTCHPAK 1012 polyester backing (3M, Lot 138) with a 40 mil (1,016 $\mu$m) casting knife. The solvent in the adhesive solution was evaporated at room temperature for 30 minutes and then in an oven at 100° C. for 15 minutes. The resulting adhesive film was laminated to a release liner (SCOTCHPAK #1022, Lot 640). The resulting transdermal laminate was cut into 0.71 cm$^2$ disks for in vitro evaluation. The resulting transdermal laminate was visibly cloudy and extensive crystals were visible upon microscopic examination.

In vitro skin flux of ketorolac from this patch with 14.9% ketorolac tromethamine (10% on a ketorolac free acid basis), 8% enhancer (propylene glycol/isopropyl myristate), and 77% adhesive solids was 7.5±2.2 $\mu$g/cm$^2$/h (Mean±SD, n=2/10 skins/diffusion cells). The average cumulative amount of ketorolac released after 24 hours was 171.6±49.0 $\mu$g/cm$^2$. The ketorolac flux from these systems is 30% of the flux observed with the system prepared with the free acid in Example 2A of U.S. Pat. No. 5,589,498. Thus, the teaching of U.S. Pat. No. 5,589,498 appears to be incorrect when applied to the use of ketorolac tromethamine salt. The salt form cannot be readily substituted for the free acid form because the skin flux performance of the resulting patch is significantly reduced.

The results in this example indicate that ketorolac free acid and the ketorolac tromethamine salt give substantially different results when used in an organic solvent-based pressure sensitive acrylic adhesive. The salt form cannot be readily substituted for the free acid form because the resulting pressure sensitive adhesive laminate contains undissolved drug crystals and the skin flux performance of the resulting patch is reduced. The teaching of U.S. Pat. No. 5,589,498 appears valid for use of the ketorolac free acid, but is inoperative when applied to the use of ketorolac tromethamine salt. In contrast, the results in Example 5 of the present application show that using the process described in the present invention, it is possible to make physically stable hydrophobic pressure sensitive adhesive matrix systems using the ketorolac tromethamine salt and that these matrix systems in fact have improved skin flux relative to systems made using the conventional technique of combining the hydrophobic free acid and an organic solvent-based adhesive.

EXAMPLE 7

Diclofenac is an acidic non-steroidal anti-inflammatory drug. The FDA-approved form of diclofenac is the hydrophilic sodium salt. Pressure sensitive matrix systems with diclofenac free acid and diclofenac sodium were prepared in an organic solvent-based acrylic/vinylpyrrolidone copolymer adhesive, TSR, at molar concentrations equivalent to 1% or 2% (w/w) of diclofenac sodium. The sodium salt was not sufficiently soluble in the organic solvent system to dissolve completely, and the dried matrix contained crystallized drug in an acrylic adhesive matrix. The free acid of diclofenac completely dissolved in the organic solvent system, and the final dried cast was visually free of drug crystals. Pressure sensitive adhesive matrix patches containing 1% or 2% (w/w) diclofenac sodium also were prepared with water-based dispersions of comparable hydrophobic acrylic copolymer adhesives, NACOR 72-9965 and ROBOND PS20 (Rohm & Haas, Philadelphia, Pa.). The dried matrices prepared using the salt and the water-based adhesives were physically stable and visually free of drug crystals. For the ROBOND PS20 adhesive it was necessary to add a thickening agent, 2% (w/w) of a vinylpyrrolidone homopolymer (KOLLIDON 90; BASF, Parsippany, N.J.) to achieve a viscosity adequate for wet film casting of the matrix. The results of in vitro skin flux experiments using these systems are summarized in Tables 9 and 10.

TABLE 9

| Skin | No. Cells | In vitro Permeation of Diclofenac[a] | | |
|---|---|---|---|---|
| | | TSR/salt[b] | TSR/acid[c] | NACOR/salt[d] |
| 1 | 5 | 0.87 ± 0.29 | 1.18 ± 0.13 | 4.40 ± 0.69 |
| 2 | 5 | 0.93 ± 0.45 | 0.97 ± 0.26 | 9.47 ± 2.92 |
| 3 | 5 | 0.60 ± 0.12 | 0.59 ± 0.14 | 7.38 ± 1.31 |
| 4 | 5 | 2.52 ± 1.07 | 1.47 ± 1.14 | 10.90 ± 6.18 |
| Total | 20 | 1.23 ± 0.95 | 1.05 ± 0.64 | 8.04 ± 4.07 |

[a]Mean ± SD, $\mu g/(cm^2 \ast 24\ h)$
[b]TSR/diclofenac sodium = 99%/1% (w/w)
[c]TSR/diclofenac free acid = 99.1%/0.9% (w/w)
[d]NACOR 72-9965/diclofenac sodium 99%/1% (w/w)

TABLE 10

| Skin | No. Cells | In vitro Permeation of Diclofenac[a] | | |
|---|---|---|---|---|
| | | TSR/salt[b] | TSR/acid[c] | ROBOND/salt[d] |
| 1 | 5 | 1.1 ± 0.2 | 2.5 ± 0.3 | 28.1 ± 5.4 |
| 2 | 5 | 0.5 ± 0.2 | 1.0 ± 0.2 | 14.3 ± 6.4 |
| 3 | 5 | 1.4 ± 1.4 | 3.4 ± 1.5 | 22.2 ± 3.8 |
| Total | 15 | 1.0 ± 0.9 | 2.3 ± 1.3 | 21.5 ± 7.6 |

[a]Mean ± SD, $\mu g/(cm^2 \ast 24\ h)$
[b]TSR/diclofenac sodium = 98%/2% (w/w)
[c]TSR/diclofenac = 98.2%/1.8% (w/w)
[d]ROBOND PS20/KOLLIDON 90/diclofenac Na = 96%/2%/2% (w/w)

In vitro permeation from the matrix prepared with the sodium salt of diclofenac and the water based adhesives was significantly greater than that from the systems prepared with the organic solvent-based adhesive. These results demonstrate that pressure sensitive matrix films can be prepared using the technique of combining the hydrophilic sodium salt form of diclofenac and water based adhesive dispersion. The matrix systems manufactured in this manner exhibit significantly improved skin flux relative to systems containing undissolved drug crystals manufactured by combining the tromethamine salt with a comparable solvent-based adhesive. In addition, the matrix systems manufactured using the sodium salt and the water-based adhesive dispersion had skin flux rates which were unexpectedly 8 to 9-fold higher on average than the skin flux from systems produced using the conventional technique of combining the hydrophobic free acid form with a comparable organic solvent-based pressure sensitive adhesive.

The systems manufactured with the salt and the water-based adhesive dispersions were stored at room temperature and examined using optical microscopy at 100× magnification for the presence of drug crystals. No crystals were observed after 101 weeks of storage, indicating that these are physically stable systems.

EXAMPLE 8

Warfarin is a widely prescribed anticoagulant. The free drug form contains a conjugated alcohol and alkene, which can be used to make a hydrophilic sodium salt through formation of an enolate anion. This sodium salt is the form of the drug approved for oral administration. Matrix systems were prepared using the free drug form and an organic solvent-based adhesive solution and using the salt form and a comparable aqueous dispersion acrylic copolymer adhesive. Warfarin free drug at 12% (w/w) was incorporated in an organic solvent-based acrylic/vinylpyrrolidone copolymer adhesive (TSR). The hydrophobic free drug dissolved readily in the organic solvents and the resulting dry film was free from drug crystals, visible and microscopic. A comparable formulation was prepared with 12% sodium warfarin and a water-based dispersion of a comparable acrylic copolymer adhesive (Nacor 72-9965) thickened with 5.0 % (w/w) of a polyvinylpyrrolidone homopolymer (Kollidon 90F). The hydrophilic warfarin sodium salt dissolved readily in water-based dispersion and the resulting dry hydrophobic matrix has been free from visible and microscopic drug crystals. The results of in vitro skin permeation experiments using these systems are shown in Table 11.

TABLE 11

| Skin | No. Cells | In vitro Permeation of Warfarin[a] | |
|---|---|---|---|
| | | TSR/base[b] | Nacor/salt[c] |
| 1 | 5 | 40.3 ± 5.6 | 35.0 ± 5.1 |
| 2 | 5 | 73.3 ± 14.0 | 64.0 ± 14.8 |
| 3 | 5 | 26.0 ± 8.3 | 30.5 ± 14.0 |
| Total | 15 | 46.5 ± 24.3 | 43.2 ± 18.2 |

[a]Mean ± SD, $\mu g/(cm^2 \ast 24\ h)$
[b]TSR/Warfarin = 88/12% (w/w)
[c]Nacor 72-9965/Warfarin Na/Kollidon 90 = 83/12/5% (w/w)

As shown in Table 11, in vitro permeation of warfarin for the system prepared by mixing the hydrophilic salt and a water-based dispersion of a hydrophobic pressure sensitive adhesive is comparable to that obtained using the conventional technique of combining the hydrophobic free drug form and a comparable organic solvent-based hydrophobic adhesive. This result contrasts with the results in Examples 5 and 7 in which systems made by combining the sodium and tromethamine salts of drugs containing a carboxylic acid group and a water-based PSA dispersion exhibited greatly increased flux rates relative to comparable systems made by combining the free acid form and an organic solvent-based PSA. This indicates that there is an unusual skin flux enhancing effect observed when the manufacturing technique is applied to cationic salts of carboxylic acid containing drugs, but such flux enhancement is not observed when cationic salts of other anionic drug species are used.

EXAMPLE 9

Lidocaine is an analgesic drug that is pharmaceutically approved in both the hydrophilic hydrochloride salt form and the hydrophobic free base forms. Pressure sensitive matrix systems with lidocaine free base and lidocaine HCl were prepared in an organic solvent-based hydrophobic acrylic copolymer adhesive, DURO-TAK 2516, at concentrations equivalent to 1% (w/w) of the HCl salt. The free base dissolved easily in the organic solvent solution and the resulting dried matrix was visibly free of drug crystals. The HCl salt did not dissolve completely in the organic solvent-based adhesive, and the final dried cast contains visible solid drug crystals in the adhesive matrix. A matrix system with lidocaine HCl at 1% (w/w) was also prepared in a comparable water-based acrylic adhesive, NACOR 72-9965. The dried matrix produced using the salt and the water-based adhesive dispersion was physically stable and free of drug crystals. The results of in vitro skin flux experiments using these systems are summarized in Table 12.

TABLE 12

| Skin | No. Cells | In vitro Permeation of Lidocaine[a] | | |
|---|---|---|---|---|
| | | TSR/salt[b] | TSR/base[c] | NACOR/salt[d] |
| 1 | 5 | 2.97 ± 0.35 | 24.01 ± 2.53 | 12.14 ± 1.87 |
| 2 | 5 | 6.75 ± 2.24 | 23.15 ± 2.76 | 11.11 ± 2.16 |
| 3 | 5 | 6.49 ± 1.77 | 33.30 ± 2.10 | 14.73 ± 3.31 |
| 4 | 5 | 10.07 ± 2.99 | 32.73 ± 2.32 | 21.34 ± 2.32 |
| Total | 20 | 6.57 ± 3.20 | 28.30 ± 5.35 | 14.83 ± 4.68 |

[a]Mean ± SD, $\mu g/(cm^2 \ast 24\ h)$
[b]TSR/lidocaine HCl 99%/1% (w/w)
[c]TSR/lidocaine free base = 99.14%/0.86% (w/w)
[d]NACOR 72-9965/lidocaine HCl 99%/1% (w/w)

Permeation with the physically stable, crystal-free matrix prepared with the salt form of the drug and the water-based adhesive was greater than that obtained with the matrix containing a mixture of dissolved and crystallized drug produced using the salt and the organic solvent-based adhesive. The flux from the matrix system prepared using the salt and the water-based adhesive dispersion was also comparable to the flux from the matrix prepared with the free base form of the drug and the organic solvent-based adhesive. These results demonstrate that it is feasible to manufacture effective hydrophobic pressure sensitive adhesive patches by combining the hydrophilic lidocaine hydrochlolride salt and a water-based dispersion of a hydrophobic pressure sensitive adhesive.

EXAMPLE 10

Clonidine is an antihypertensive drug approved for oral administration as the hydroride salt and for transdermal delivery as the free base. In these transdermal systems, conversion to the free base form was required because the salt form was insoluble in the organic solvent-based polyisobutylene adhesive used in the transdermal patch. In the instant example, a pressure sensitive adhesive matrix system with clonidine free base at a concentration equivalent to 2% (w/w) of the HCl salt was prepared in a polyisobutylene adhesive blend that had been dissolved in organic solvents, 33% high molecular weight PIB (VISTANEX MM L-100) and 66% low molecular weight PIB (VISTANEX LM-MH), both from Exxon (Houston, Tex.). The hydrophobic free base dissolved readily in the organic solvent solution and the resulting dry matrix film was free from drug crystals. Another matrix system with clonidine HCl at 2% (w/w) was prepared in similar polymers which had been dispersed in a water, 33% high molecular weight PIB (PIB 500) and 66% low molecular weight PIB (BUTYL 100), both from Lord Corporation (Pompano Beach, Fla.). The dried pressure sensitive adhesive matrix prepared with the hydrophilic salt and the water-based polymer dispersion was visibly free of drug crystals. The results of in vitro skin flux experiments using these systems are summarized in Table 13.

TABLE 13

| Skin | No. Cells | In vitro Permeation of Clonidine[a] | |
|---|---|---|---|
| | | VISTANEX/base[b] | LORD/salt[c] |
| 1 | 5 | 8.6 ± 5.7 | 13.2 ± 6.1 |
| 2 | 4 | 14.0 ± 4.0 | 7.2 ± 0.9 |
| Total | 9 | 11.0 ± 5.5 | 10.5 ± 5.3 |

[a]Mean ± SD, $\mu g/(cm^2 \ast 24\ h)$
[b]VISTANEX L-100/LM-MH/clonidine = 33.1/65.2/1.7% (w/w)
[c]LORD PIB-500/BL-100/clonidine HCl = 33%/65%/2% (w/w)

Permeation with the matrix prepared with the salt form of the drug and the water-based PID dispersion was comparable to that obtained with the matrix prepared using the more conventional technique with the free base form of the drug and the organic solvent-based PIB solution. These results demonstrate that it is feasible to manufacture physically stable, effective transdermal systems by mixing a hydrophilic salt form of a drug with a hydrophobic polyisobutylene dispersion and evaporating the water phase.

EXAMPLE 11

Permeation enhancers can optionally be incorporated when matrix systems are prepared using water-based hydrophobic adhesive dispersions and hydrophilic drug salts. This example illustrates the incorporation of enhancers for an acidic drug (diclofenac sodium) and two basic drugs (buspirone HCl and clonidine HCl). Pressure sensitive adhesive matrix systems were prepared with the salt forms of these drugs at a concentration of 2% (w/w) in a water-based acrylic adhesive, NACOR 72-9965. Additional systems were also prepared with 2.5% (w/w) of a non-ionic permeation enhancer, lauryl lactate (CERAPHYL 31; ISP, Van Dyk, N.J.). The results of in vitro skin flux experiments with these systems are shown in Tables 14–16.

TABLE 14

| Skin | No. Cells | In vitro Permeation of Diclofenac[a] | |
|---|---|---|---|
| | | NACOR/salt[b] | NACOR/salt/enhancer[c] |
| 1 | 5 | 20.73 ± 1.72 | 30.47 ± 8.23 |
| 2 | 5 | 2.13 ± 0.44 | 3.40 ± 0.82 |
| Total | 10 | 11.43 ± 9.87 | 16.94 ± 15.29 |

[a]Mean ± SD, $\mu g/(cm^2 \ast 24\ h)$
[b]NACOR 72-9965/diclofenac sodium = 98%/2% (w/w)
[c]NACOR 72-9965/diclofenac sodium/lauryl lactate = 95.5%/2%/2.5% (w/w)

TABLE 15

| Skin | No. Cells | In vitro Permeation of Buspirone[a] | |
|---|---|---|---|
| | | NACOR/salt[b] | NACOR/salt/enhancer[c] |
| 1 | 5 | 2.60 ± 0.97 | 4.20 ± 1.76 |
| 2 | 5 | 37.91 ± 2.50 | 48.28 ± 3.60 |
| Total | 10 | 20.26 ± 18.70 | 26.24 ± 23.38 |

[a]Mean ± SD, $\mu g/(cm^2 \ast 24\ h)$
[b]NACOR 72-9965/buspirone HCl = 98%/2% (w/w)
[c]NACOR 72-9965/buspirone HCl/lauryl lactate = 95.5%/2%/2.5% (w/w)

TABLE 16

| Skin | No. Cells | In vitro Permeation of Clonidine[a] | |
|---|---|---|---|
| | | NACOR/salt[b] | NACOR/salt/enhancer[c] |
| 1 | 5 | 3.0 ± 0.7 | 3.7 ± 1.1 |
| 2 | 5 | 12.8 ± 5.7 | 15.4 ± 9.4 |
| Total | 10 | 8.5 ± 6.6 | 9.6 ± 8.8 |

[a]Mean ± SD, μg/(cm²*24 h)
[b]NACOR 72-9965/clonidine HCl = 98%/2% (w/w)
[c]NACOR 72-9965/clonidine HCl/lauryl lactate = 95.5%/2%/2.5% (w/w)

The results of these experiments illustrate that effective amounts of permeation enhancers can be incorporated advantageously into water-based adhesive matrix systems.

EXAMPLE 12

Additional examples of the incorporation of permeation enhancers were prepared using clonidine hydrochloride as a model drug in two different water-based adhesive dispersions. Pressure sensitive adhesive matrix systems were prepared by combining clonidine hydrochloride salt sufficient to give a concentration of 2%(w/w) in the dried film with the following water-based adhesive dispersions: (1) Morstick 214 (Morton International, Taylors, S.C.), a hydrophobic acrylic copolymer adhesive dispersion; and (2) EVA-TAK 33-4060 (National Starch and Chemical), an ethylene-vinylacetate copolymer adhesive dispersion. Comparable enhanced formulation were prepared by combining the drug and water-based adhesive dispersion mixture with a known permeation enhancer, lauroyl lactylic acid (R.I.T.A. Corporation Woodstock, Ill.) in amounts sufficient to obtain a concentration of 2.4% (w/w) enhancer in the dried film. All systems were thickened for film casting with a polyvinylpyrrolidone copolymer at 5% (w/w), (Collacral VL30, B.A.S.F., Ludwigshafen am Rhein, Germany). The results of in vitro skin flux experiments with these systems are shown in Tables 17–18.

TABLE 17

| Skin | No. Cells | In vitro Permeation of Clonidine[a] | |
|---|---|---|---|
| | | Morstick/salt[b] | Morstick/salt/enhancer[c] |
| 1 | 5 | 10.3 ± 6.5 | 11.4 ± 5.0 |
| 2 | 5 | 1.2 ± 0.7 | 5.8 ± 1.0 |
| 3 | 5/4 | 2.8 ± 2.7 | 12.5 ± 3.0 |
| 4 | 5 | 3.0 ± 2.2 | 7.5 ± 1.5 |
| Total | 20/19 | 4.3 ± 4.0 | 9.3 ± 3.2 |

[a]Mean ± SD, μg/(cm²*24 h)
[b]Morstick 214/clonidine HCl/Collacral VL30 = 93%/2%/5% (w/w)
[c]Morstick 214/clonidine HCl/Collacral VL30/Lauroyl Lactylic Acid = 90.6/2/5/2.4% (w/w)

TABLE 18

| Skin | No. Cells | In vitro Permeation of Clonidine[a] | |
|---|---|---|---|
| | | EVA-TAK/salt[b] | EVA-TAK/salt/enhancer[c] |
| 1 | 5 | 20.9 ± 3.0 | 23.8 ± 5.0 |
| 2 | 4/5 | 12.8 ± 7.3 | 48.0 ± 6.6 |

TABLE 18-continued

| Skin | No. Cells | In vitro Permeation of Clonidine[a] | |
|---|---|---|---|
| | | EVA-TAK/salt[b] | EVA-TAK/salt/enhancer[c] |
| 3 | 5 | 26.1 ± 18.9 | 25.4 ± 3.8 |
| 4 | 5 | 5.9 ± 1.5 | 15.5 ± 9.0 |
| Total | 19/20 | 16.4 ± 8.9 | 28.2 ± 13.9 |

[a]Mean ± SD, μg/(cm²*24 h)
[b]EVA-TAK/clonidine HCl/Collacral VL30 = 93%/2%/5% (w/w)
[c]EVA-TAK/clonidine HCl/Collacral VL30/Lauroyl Lactylic Acid = 90.6/2/5/2.4% (w/w)

The results of these experiments illustrate that effective amounts of permeation enhancers con be incorporated advantageously into water-based hydrophobic acrylic copolymer adhesives and water-based ethylene-vinyl acetate copolymer adhesives.

EXAMPLE 13

An additional example of the incorporation of a permeation enhancer in a water-based adhensive was prepared using buspirone HCl as a model drug and sucrose laurate, a known permeation enhancer. Pressure sensitive adhesive matrix systems were prepared with buspirone HCl at a concentration of 2% (w/w) and sucrose laurate at 5% (w/w) (Ryoto LWA 1570; Mitubishi-Kagaku Foods Corporation, Tokyo, Japan) was mixed with a water-based acrylic adhensive, NACOR 72-9965. The results of in vitro skin flux experiments with this system are shown in Table 19.

TABLE 19

| Skin | No. Cells | In Vitro Permeation of Buspirone[a] NACOR/salt/enhancer[b] |
|---|---|---|
| 1 | 5 | 23.0 ± 3.5 |
| 2 | 5 | 14.2 ± 1.0 |
| 3 | 5 | 53.6 ± 8.9 |
| 4 | 5 | 23.7 ± 6.6 |
| Total | 20 | 28.6 ± 16.2 |

[a]Mean ± SD, μg/(cm²*24 h)
[b]NACOR 72-9965/buspirone HCl/Ryoto LWA 1570 = 93/2/5%

These results further illustrate that permeation enhancers may be readily incorporated into a water-based adhesive matrix system.

We claim:

1. A method of preparing a pressure sensitive adhesive matrix patch device comprising the steps of:
    a) dissolving an effective amount of a hydrophilic salt form of a drug in an aqueous dispersion of a hydrophobic pressure sensitive adhesive and optionally a permeation enhancer, to form a mixture;
    b) film casting said mixture and evaporating a water phase of the aqueous dispersion to obtain a hydrophobic pressure sensitive adhesive matrix film in which said drug is fully dissolved and having first and second surfaces thereof; and
    c) laminating a release liner to said first surface of said matrix film and a substantially drug-impermeable backing layer to said second surface.

2. The method of claim 1 wherein said hydrophobic adhesive is a member selected from the group consisting of acrylic, polyisobutylene, and ethylene-vinylacetate adhesives.

3. The method of claim 1 wherein said hydrophilic salt form of said drug is a member selected from the group consisting of sodium diclofenac, sodium cromolyn, sodium acyclovir, sodium ampicillin, sodium warfarin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, and brompheniramine maleate.

4. The method of claim 1 wherein said drug is an azapirone salt.

5. The method of claim 1 wherein said hydrophobic adhesive is an acrylic adhesive.

6. The method of claim 5 wherein said drug is a member selected from the group consisting of albuterol sulfate, ketorolac tromethamine, diclofenac sodium, buspirone HCl, lidocaine HCl, clonidine HCl, and warfarin sodium.

7. The method of claim 6 wherein said adhesive matrix film comprises a permeation enhancer selected from the group consisting of cell envelope disordering compounds, solvents, and mixtures thereof.

8. The method of claim 6 wherein said drug is ketorolac tromethamine.

9. The method of claim 6 wherein said drug is diclofenac sodium.

10. The method of claim 6 wherein said drug is buspirone HCl.

11. The method of claim 6 wherein said drug is lidocaine HCl.

12. The method of claim 6 wherein said drug is clonidine HCl.

13. The method of claim 6 wherein said drug is warfarin sodium.

14. The method of claim 6 wherein said drug is albuterol sulfate.

15. The method of claim 3 wherein said hydrophobic adhesive is a polyisobutylene adhesive.

16. The method of claim 15 wherein said drug is clonidine HCl.

17. The method of claim 16 wherein said adhesive matrix film comprises a permeation enhancer selected from the group consisting of cell envelope disordering compounds, solvents, and mixtures thereof.

18. The method of claim 15 wherein said drug is buspirone HCl.

19. The method of claim 18 wherein said adhesive matrix film comprises a permeation enhancer selected from the group consisting of cell envelope disordering compounds, solvents, and mixtures thereof.

20. A pressure sensitive adhesive matrix patch device for transdermal delivery of a drug, wherein said device is prepared according to the method of claim 1.

21. A method of inhibiting crystallization of a drug in a pressure sensitive adhesive matrix patch wherein said drug is intimately admixed with a hydrophobic pressure sensitive adhesive comprising the steps of:
   a) dissolving an effective amount of a hydrophilic salt form of the drug with an aqueous dispersion of the hydrophobic pressure sensitive adhesive to form a mixture;
   b) film casting said mixture and evaporating a water phase of the aqueous dispersion to obtain a hydrophobic pressure sensitive adhesive matrix having said drug fully dissolved therein and having first and second surfaces thereof; and
   c) laminating a release liner to said first surface of said matrix film and a substantially drug-impermeable backing layer to said second surface.

22. The method of claim 21 wherein said adhesive is a member selected from the group consisting of acrylic, polyisobutylene, and ethylene-vinylacetate adhesives.

23. The method of claim 21 wherein said hydrophilic salt form of said drug is a member selected from the group consisting of sodium diclofenac, sodium cromolyn, sodium acyclovir, sodium ampicillin, sodium warfarin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, and brompheniramine maleate.

24. The method of claim 21 wherein said drug is an azapirone salt.

25. The method of claim 22 wherein said adhesive is an acrylic adhesive.

26. The method of claim 25 wherein said drug is a member selected from the group consisting of albuterol sulfate, ketorolac tromethamine, diclofenac sodium, buspirone HCl, lidocaine HCl, clonidine HCl, and warfarin sodium.

27. The method of claim 26 wherein said matrix film further comprises an effective amount of a permeation enhancer selected from the group consisting of cell envelope disordering compounds, solvents, and mixtures thereof.

28. The method of claim 26 wherein said drug is ketorolac tromethamine.

29. The method of claim 26 wherein said drug is diclofenac sodium.

30. The method of claim 26 wherein said drug is buspirone HCl.

31. The method of claim 26 wherein said drug is lidocaine HCl.

32. The method of claim 26 wherein said drug is clonidine HCl.

33. The method of claim 26 wherein said drug is warfarin sodium.

34. The method of claim 26 wherein said drug is albuterol sulfate.

35. The method of claim 22 wherein said adhesive is a polyisobutylene adhesive.

36. The method of claim 35 wherein said drug is clonidine HCl.

37. The method of claim 36 wherein said matrix film further comprises a permeation enhancer selected from the group consisting of cell envelope disordering compounds, solvents, and mixtures thereof.

38. The method of claim 35 wherein said drug is buspirone HCl.

39. The method of claim 38 wherein said matrix film further comprises a permeation enhancer selected from the group consisting of cell envelope disordering compounds, solvents, and mixtures thereof.

40. A method of increasing transdermal flux of an acidic drug comprising applying a pressure sensitive matrix patch to skin, wherein said matrix patch is prepared by the steps comprising:

a) dissolving an effective amount of a hydrophilic salt form of the acidic drug with an aqueous dispersion of a hydrophobic pressure sensitive adhesive to form a mixture;

b) film casting said mixture and evaporating a water phase of the aqueous dispersion to obtain a hydrophobic pressure sensitive adhesive matrix film having said acidic drug fully dissolved therein and having first and second surfaces thereof; and c) laminating a release liner to said first surface of said matrix film and a substantially drug-impermeable backing layer to said second surface.

41. The method of claim 40 wherein said adhesive is a member selected from the group consisting of acrylic, polyisobutylene, and ethylene-vinylacetate adhesives.

42. The method of claim 40 wherein said hydrophilic salt form of said acidic drug is a member selected from the group consisting of sodium diclofenac, sodium cromolyn, sodium ampicillin, and ketorolac tromethamine.

43. The method of claim 42 wherein said hydrophilic salt of said acidic drug is sodium diclofenac and said adhesive is an acrylic adhesive.

44. The method of claim 42 wherein said hydrophilic salt of said acidic drug is ketorolac tromethamine and said adhesive is an acrylic adhesive.

45. The method of claim 40 wherein said matrix film further comprises an effective amount of a permeation enhancer selected from the group consisting of cell envelope disordering compounds, solvents, and mixtures thereof.

46. A method of preparing a drug/adhesive layer of a pressure sensitive adhesive matrix patch device comprising the steps of:

a) dissolving an effective amount of a hydrophobic salt form of a drug with an aqueous dispersion of a hydrophobic pressure sensitive adhesive and optionally a permeation enhancer to form a mixture; and b) film casting said mixture and evaporating a water phase of the aqueous dispersion to obtain a hydrophobic pressure sensitive adhesive matrix film in which said drug is fully dissolved.

47. A method of inhibiting crystallization of a drug in a drug/adhesive layer of a pressure sensitive adhesive matrix patch comprising the steps of:

a) dissolving an effective amount of a hydrophilic salt form of a drug in an aqueous dispersion of the hydrophobic pressure sensitive adhesive to form a mixture; and b) film casting said mixture and evaporating a water phase of the aqueous dispersion to obtain a hydrophobic pressure sensitive matrix film having said drug fully dissolved therein.

48. A method of preparing a pressure sensitive adhesive comprising the steps of:

a) dispersing a hydrophobic pressure sensitive adhesive in an aqueous solution to form an aqueous dispersion having a water phase;

b) dissolving an effective amount of a hydrophilic salt form of a drug in the water phase to form a mixture of drug and adhesive;

c) film casting said mixture and removing the water phase to obtain a hydrophobic pressure sensitive adhesive matrix film in which said drug is dissolved.

* * * * *